United States Patent
Olbert et al.

(10) Patent No.: US 7,381,851 B2
(45) Date of Patent: Jun. 3, 2008

(54) METHOD FOR PRODUCING FORMALDEHYDE

(75) Inventors: Gerhard Olbert, Dossenheim (DE);
Thorsten Johann, Limburgerhof (DE);
Markus Weber, Ludwigshafen (DE);
Neven Lang, Mannheim (DE);
Eckhard Ströfer, Mannheim (DE);
Martin Fiene, Niederkirchen (DE);
Markus Siegert, Heidelberg (DE)

(73) Assignee: BASF Aktiengesellschaft (DE)

( * ) Notice: Subject to any disclaimer, the term of this patent is extended or adjusted under 35 U.S.C. 154(b) by 91 days.

(21) Appl. No.: 10/581,986

(22) PCT Filed: Dec. 23, 2004

(86) PCT No.: PCT/EP2004/014672

§ 371 (c)(1),
(2), (4) Date: Jun. 7, 2006

(87) PCT Pub. No.: WO2005/063375

PCT Pub. Date: Jul. 14, 2005

(65) Prior Publication Data

US 2007/0142677 A1    Jun. 21, 2007

(30) Foreign Application Priority Data

Dec. 23, 2003   (DE) .............................. 103 61 517

(51) Int. Cl.
*C07C 45/29*   (2006.01)

(52) U.S. Cl. ................ 568/472; 568/474; 568/487

(58) Field of Classification Search ................ None
See application file for complete search history.

(56) References Cited

U.S. PATENT DOCUMENTS 3,152,997 A   10/1964   Natta et al.
3,420,783 A   1/1969   Bergstrand

FOREIGN PATENT DOCUMENTS

| DE | 100 31 347 | 1/2001 |
|---|---|---|
| EP | 1 153 653 | 11/2001 |
| EP | 1 477 220 | 11/2004 |
| GB | 1080508 | 8/1967 |
| WO | WO-02/068110 | 9/2002 |

OTHER PUBLICATIONS

Exner, W. et al., "Das Hiag/Lurgi-Formaldehyd-Verfahren", CAV (1973), pp. 87-92.

*Primary Examiner*—Sikarl A. Witherspoon
(74) *Attorney, Agent, or Firm*—Connolly Bove Lodge & Hutz

(57) ABSTRACT

A process for preparing formaldehyde by gas-phase oxidation of methanol vapor by means of a gas stream comprising molecular oxygen in the presence of a fixed-bed catalyst comprising iron and molybdenum, wherein the process is carried out in a reactor (1) having heat-exchange plates (2) which are arranged in the longitudinal direction of the reactor (1) and have a spacing between them and through which a heat transfer medium flows, inlet and outlet facilities (3, 4) for the heat transfer medium to the heat-exchange plates (2) and also gaps (5) between heat-exchange plates (2) in which the fixed-bed catalyst is present and into which the methanol vapor and the gas stream comprising molecular oxygen are passed, is described.

17 Claims, 11 Drawing Sheets

A-A

A-A

A-A

9

4

9

3

2

5

METHOD FOR PRODUCING FORMALDEHYDE

RELATED APPLICATIONS

This application is a national stage application (under 35 U.S.C. 371) of PCT/EP2004/014672 filed Dec. 23, 2004, which claims benefit to German application 103 61 517.2 filed Dec. 23, 2003.

The invention relates to a process for preparing formaldehyde by gas-phase oxidation of methanol vapor by means of gas stream comprising molecular oxygen in the presence of a fixed-bed catalyst comprising iron and molybdenum.

The industrial processes for preparing formaldehyde from methanol are based on two different process principles, firstly dehydrogenation or oxydehydrogenation of methanol over silver or copper catalysts, also known as the silver contact process, and secondly oxidation of methanol in the presence of iron-containing molybdenum oxide catalysts, known as, in particular, the Formox process.

In the following, the term Formox process will be used for processes for preparing formaldehyde by oxidation of methanol in the presence of iron-containing molybdenum oxide catalysts.

Since 1921, many such processes have been developed. Use is frequently made of catalysts which have an atomic ratio of molybdenum to iron of from 1.0 to 5.0 and may further comprise small amounts of additional oxides such as $V_2O_5$, CuO, $Cr_2O_3$, CoO and $P_2O_5$.

DE-A 1 144 252 describes, for example, an unsupported catalyst which comprises from 78 to 81% by weight of molybdenum(VI) oxide and from 18 to 19% by weight of iron(III) oxide and is prepared under carefully controlled process conditions: an iron molybdate is precipitated from a mixture of aqueous solutions of a molybdate and an iron salt, the precipitate is washed with water to remove the soluble salts until the chlorine content of the filter cake is less than 0.13 g of chlorine per 100 g of molybdenum. This precipitate is filtered off and dried to a water content of from 40 to 50%. The filter cake obtained in this way is broken up, subjected to a mechanical treatment and then converted into pellet form. The pellets are dried and finally activated by means of a progressive thermal treatment, with the temperature firstly being increased from 100° C. to 400-450° C. over a period of not less than 4 hours and this final temperature being maintained for at least another 4 hours. This is said to achieve, in particular, an improved mechanical strength, namely a mean fracture load of 7.4 kg per cylindrical pellet having a diameter and a height of 3.5 mm in each case. In the published specification mentioned, it is said that the catalyst is therefore transportable.

A further process for preparing catalysts for the Formox process is described in GB-B 1,080,508. This process, too, has very precise directions: an iron molybdate catalyst is used as starting material, this is finely milled, if appropriate after drying, to give a base powder which is mixed with water to form a mass containing from 37 to 39% by weight of water and this mass is subsequently pelletized within a period of 90 minutes, preferably within a period of 1 hour, after mixing of the base powder with water. The catalyst obtained displays, in particular, a relatively small increase in the pressure drop during use compared to known catalysts.

An improved catalyst for the Formox process has been developed by Hiag-Werke AG in 1963-1966 under the name FOX-HIAG®. This catalyst is characterized by a particular method of shaping and production. Although the contents of iron and of molybdenum (18-19% of $Fe_2O_3$ and 81-82% of $MoO_3$) are in the known ranges, the FOX-HIAG catalyst is not a mixture of the oxides but a definite compound having the hypothetical empirical formula $Fe_2Mo_3O_{18}$, which is thus different from ferric molybdate $Fe_2(MoO_4)_3$. To prepare this defined compound, it is necessary to adhere to precisely defined reaction conditions which require very careful production control. The FOX-HIAG® catalyst has an average fracture load of about 45 $kg/cm^2$. The optimum working temperature is about 350° C., with temperature peaks above 400° C. having to be avoided by means of appropriate removal of heat.

Nevertheless, the life of the FOX-HIAG® catalyst, too, is limited and is, depending on the mechanical stress, up to two years. The duration of a period of operation is, depending on the mechanical stress, up to one year. After this time of operation, the pressure increase in the reactor has generally become so great that an economical throughput can no longer be achieved. For this reason, fine catalyst particles are separated off through a screen having a mesh opening of 3 mm and the remaining larger particles are, after being supplemented by the missing amount of about 20%, recycled for a further charge (cf. "Das HIAG/Lurgi-Formaldehydverfahren" in CAV 1973, June).

However, the mechanical strength of the catalysts suitable for the Formox process still remains problematical. In particular at elevated temperature, frequently above 350° C., in particular above 400° C., the catalyst is damaged mechanically and disintegration of the catalyst particles occurs. This leads to increased pressure drops in the reaction tubes. As a result, less reaction mixture flows through the reaction tubes, and convective heat transport becomes poorer so that the temperature in the reaction tubes rises. This is also a safety risk, since overheating and in an extreme case destruction of the reactor can occur.

As reactors for the Formox process, use has hitherto generally be made of shell-and-tube apparatuses with fixed beds of catalyst in the tubes and a cooling liquid flowing around the tubes to remove the heat of reaction.

An upper limit is imposed on the diameter of the tubes by the removal of the heat of reaction via the heat transfer medium circulating between the tubes: if the diameter of the catalyst tubes is too large, the heat of reaction can no longer be removed sufficiently and local temperature increases known as hot spots which lead to damage to the catalyst, in particular to ageing, to a reduction in the mechanical stability and to a reduction in the catalyst activity and selectivity, occur in the tubes. The tubes therefore have to have a small diameter, in general in the range from 10 to 40 mm, preferably from 10 to 20 mm, in particular from 13 to 17 mm. Since the total number of tubes to be accommodated in a reactor is limited by manufacturing considerations, in particular welding considerations and stability reasons, the capacity of shell-and-tube reactors is generally limited to a maximum of from 40 000 to 50 000 tubes. The reactor experiences a further limitation as a result of the catalyst having to be partially poisoned or diluted with inert material to prevent hot spots. As a result, the space-time yield of the reaction is "artificially" reduced.

Shell-and-tube reactors have the further disadvantage that an isothermal temperature profile over the reactor cross section is possible to only a limited extent, i.e. temperature differences over the reactor cross section cannot be completely evened out. However, it is known that radial temperature differences in the heat transfer medium or coolant stream lead to an increase in the temperature of hot spots. Thus, for example, it has been found that a radial temperature difference of 1° C. in the coolant leads to an increase in the hot spot temperature of from 4 to 8° C., depending on the activity of the catalyst.

In view of the above, it was an object of the invention to provide a Formox process for preparing formaldehyde-which does not have the disadvantages of the prior art and, in particular, helps alleviate the problems of hot spots and the problems of limited mechanical stability of the catalyst with the resulting safety-related consequences.

We have accordingly found a process for preparing formaldehyde by gas-phase oxidation of methanol vapor by means of a gas stream comprising molecular oxygen in the presence of a fixed-bed catalyst, wherein the process is carried out in a reactor having heat-exchange plates which are arranged in the longitudinal direction of the reactor and have a spacing between them and through which a heat transfer medium flows, inlet and outlet facilities for the heat transfer medium to the heat-exchange plates and also gaps between heat-exchange plates in which the fixed-bed catalyst is present and into which the methanol vapor and the gas stream comprising molecular oxygen are passed.

The process of the invention is not restricted in terms of the specific operating conditions for carrying out the gas-phase oxidation of methanol vapor by means of gas stream comprising molecular oxygen for preparing formaldehyde in the presence of a fixed-bed catalyst comprising iron and molybdenum. Such processes in general are referred to as Formox processes in the present text.

The process is suitable for all known fixed-bed catalysts comprising iron and molybdenum, in particular for the fixed-bed catalysts described at the outset, especially for fixed-bed catalysts having an atomic ratio of molybdenum to iron of from 1 to 5. The catalysts can be used as all-active catalysts or as supported catalysts. They are not restricted in terms of their geometry and can, in particular, be in the form of spheres, extrudates or rings.

Heat-exchange plates are plate-shaped heat exchangers, i.e. predominantly flat structures which have an interior space which is provided with inlet and outlet lines and has a small thickness relative to its area.

They are generally produced from metal sheets, frequently from steel sheets, in particular stainless steel sheets. However, depending on the application, in particular the properties of the reaction medium and of the heat transfer medium, it is possible to use special, in particular, corrosion-resistant but also coated materials. The inlet and outlet facilities for the heat transfer media are generally located at opposite ends of the heat-exchange plates. The heat transfer medium used is frequently water or else Diphyl® (mixture of from 70 to 75% by weight of diphenyl ether and from 25 to 30% by weight of biphenyl), which also partly evaporate in a boiling process; the use of other organic heat transfer media having a low vapor pressure and even ionic liquids is also possible.

The use of ionic liquids as heat transfer media is described in DE-A 103 16 418. Preference is given to ionic liquids containing a sulfate, phosphate, borate or silicate anion. Particularly useful ionic liquids are also ones which contain a monovalent metal cation, in particular an alkali metal cation, and also a further cation, in particular an imidazolium cation. Ionic liquids containing an imidazolium, pyridinium or phosphonium cation has cation are also advantageous.

Plate-shaped heat exchangers are referred to synonymously as heat-exchange plates and also heat transfer plates and heat exchanger plates.

The term heat-exchange plates is used, in particular, for heat transfer plates whose individual, usually two, metal sheets are joined by point and/or rolled seam weldings and are frequently plastically molded under hydraulic pressure to obtain a cushion shape.

The term heat-exchange plates will in the present text be used in accordance with the above definition.

In a preferred embodiment, the heat-exchange plates are arranged parallel to one another in the reactor.

In the case of cylindrical reactors, a radial arrangement of the heat-exchange plates to leave a central space and a peripheral channel to the reactor walls free is also advantageous.

The central space, which is appropriately connected to inlet and outlet facilities for the reaction medium to or from the immediate spaces between the heat-exchange plates, can in principle have any geometric shape, for example the shape of a polygon, in particular the shape of a triangle, of a square, of a preferably regular hexagon or of a preferably regular octagon and can also have an essentially circular shape.

The heat-exchange plates preferably extend in the longitudinal direction of the reactor essentially over the entire length of the cylindrical reactor with the exception of the reactor ends.

The reaction medium is preferably conveyed radially through the intermediate spaces between the heat-exchange plates.

The peripheral channel is preferably ring-shaped. It serves as collection and/or distribution chamber for the reaction medium. The peripheral channel can be separated from the intermediate spaces between the heat-exchange plates by a suitable retention device, preferably a cylindrical screen or a perforated plate; analogously, an appropriate retention device can separate the intermediate spaces between the heat-exchange plates from the central space. This embodiment is particularly useful since a reaction is being carried out using a fixed-bed catalyst which is accommodated in the intermediate spaces between the heat-exchange plates and whose discharge with the reaction medium is to be prevented by appropriate choice of the openings in the retention device.

The radial transport of the reaction medium can occur centrifugally and/or centripetally, with centrifugal transport of the reaction medium being particularly advantageous when the radial flow is in a single direction.

The radial flow of the reaction medium between the radially arranged heat-exchange plates has the advantage of a low pressure drop. Since the oxidation of methanol occurs with an increase in volume, the pressure conditions prevailing in the case of centrifugal transport are particularly advantageous because the distances between the heat-exchange plates increase toward the outside.

When the reaction medium flows radially through the spaces between the radially arranged heat-exchange plates, the heat transfer area available changes continuously. Thus, when the reaction medium is transported centrifugally, the transfer area decreases continuously going from the center to the outside. As a result, optimization of heat transfer is achieved in the present reaction with decreasing evolution of heat as the reaction progresses.

The radial extension of all heat-exchange plates is preferably identical; fitting of the heat-exchange plates to the interior wall of the reactor is thus not necessary. On the contrary, plates of a single construction type can be used.

The radial extension of the heat-exchange plates is preferably in the range from 0.1 to 0.95 of the reactor radius, particularly preferably in the range from 0.3 to 0.9 of the reactor radius.

The heat-exchange plates are essentially planar. This means that they are not completely flat structures but can be, in particular, regularly curves, folded, creased or corrugated. The heat-exchange plates are produced by known methods.

Periodically profiled structural elements, in particular corrugated plates, may preferably be present in the heat-exchange plates. Such structural elements are known as mixing elements in static mixers and are described, for example, in DE-A 19623051. In the present case, they serve, in particular, to optimize heat transfer. To match the required heat profile, it is possible to provide a higher plate density in the outer reactor region compared to the inner reactor region, in particular additional plates in the outer reactor region having a smaller radial extension compared to the other heat-exchange plates, preferably a radial extension in the range from 0.1 to 0.7, particularly preferably from 0.2 to 0.5, of the radial extension of the other heat-exchange plates. The additional plates can each have the same dimensions, but it is also possible to use two or more construction types of additional plates, with the construction types differing from one another in their radial extension and/or their length.

The additional heat-exchange plates are preferably arranged symmetrically between the other heat-exchange plates. They allow improved matching to the temperature profile of the gas-phase oxidation.

A preferred embodiment provides a reactor made up of two or more, in particular detachable, reactor sections. In particular, each reactor section is equipped with a separate heat transfer medium circuit.

The individual reactor sections can be assembled by means of flanges according to requirements. The flow of the reaction medium between two successive reactor sections is preferably achieved by means of suitable deflection plates which have a deflection and/or separation function. Multiple deflection of the reaction medium can be achieved by choosing an appropriate number of deflection plates.

It is possible to provide intermediate introduction points for the reaction medium, in particular via the peripheral channel, on one or more of the reactor sections. In this way, the reaction conditions and the temperature profile can be optimized in an advantageous manner.

It is possible to provide a reactor having a plurality of reactor sections with a single heat transfer medium circuit. However, two or more separate heat transfer medium circuits through the heat-exchange plates can also be preferred. In this way, improved matching to different heat transfer requirements as the chemical reaction progresses can be achieved.

The process is preferably carried out in a reactor which is equipped with one or more cuboidal heat-exchange plate modules which are each made up of two or more rectangular heat-exchange plates which are arranged parallel to one another so as to leave a gap between them.

Reactors containing heat-exchange plate modules are known, for example, from DE-A 103 33 866, whose disclosure is hereby fully incorporated by reference into the present patent application.

The heat-exchange plate modules are each made up of two or more rectangular heat-exchange plates which are arranged parallel to one another so as to leave a gap between them.

The heat-exchange plates are manufactured from corrosion-resistant materials, preferably stainless steel, for example steels having the material numbers 1.4541 or 1.4404, 1.4571 or 1.4406, 1.4539 and 1.4547 or other alloy steels.

The material thickness of the metal sheets used for this purpose can be from 1 to 4 mm, from 1.5 to 3 mm, from 2 to 2.5 mm or up to 2.5 mm.

In general, two rectangular metal sheets are joined along their long sides and ends to form a heat-exchange plate, with a rolled seam or lateral welding shut or a combination of the two being possible, so that the space in which the heat transfer medium is located later is sealed on all sides. The margin of the heat-exchange plates is preferably separated off at or in the lateral rolled seam of the longitudinal edge so that the poorly cooled or uncooled marginal region in which catalyst is usually also present has a very small geometric dimension.

The metal sheets are joined to one another by means of point welds distributed over the rectangular area. At least partial connection by means of straight or curved and even circular rolled seams is also possible. The volume through which the heat transfer medium flows can also be divided into a plurality of separate regions by means of additional rolled seams.

The width of the heat-exchange plates is restricted essentially by manufacturing considerations and can be from 100 to 2500 mm, or from 500 to 1500 mm. The length of the heat-exchange plates depends on the reaction, in particular on the temperature profile of the reaction, and can be from 300 to 3000 mm, or else from 500 to 1500 mm.

Two or more heat-exchange plates are arranged parallel to one another with a space between them to form a heat-exchange sheet module. This results in shaft-like gaps which, at the narrowest points between the plates, have, for example, a width of from 8 to 50 mm, preferably from 10 to 30 mm, more preferably from 13 to 20 mm, in particular 14 mm, between immediately adjacent plates.

Additional spacers can be installed between the individual heat-exchange plates of a heat-exchange plate module, e.g. in the case of large-area plates, to prevent deformation which could alter the spacing or position of the plates. To install these spacers, regions of the plates can be separated off from the flow-through region for the heat transfer medium by means of, for example, circular rolled seams so that, for example, holes for fastening screws of the spacers can be introduced into the plates.

The gaps filled with catalyst particles in a heat-exchange plate module can be sealed from one another, e.g. can be welded shut, or can have a process-side connection to one another.

To set the desired spacing on assembling the individual heat-exchange plates to form a module, the plates are fixed in position so as to fix the distance between them.

The point of welds of adjacent heat-exchange plates can be opposite one another or be offset.

In general, for manufacturing reasons, when two or more cuboidal heat-exchange plate modules are employed, they will each have the same dimensions. In the case of assemblies of 10 or 14 heat-exchange plate modules, it can be advantageous in terms of the compactness of the overall apparatus to choose two module types having different edge lengths or different edge length ratios.

Preference is given to assemblies of 4, 7, 10 or 14 heat-exchange plate modules each having the same dimensions. The visible projection of a module in the flow direction can be square, but can also be rectangular with a side ratio of 1.1 or 1.2. Combinations of 7, 10 or 14 modules having rectangular module projections so that the diameter of the outer cylindrical shell is minimized are advantageous. Particularly advantageous geometric arrangements can be achieved when, as indicated above, a number of 4, 7 or 14 heat-exchange plate modules is chosen.

The heat-exchange plate modules should advantageously be individually replaceable, for example in the case of leaks, deformations of the heat-exchange plates or in the case of problems relating to the catalyst.

The heat-exchange plate modules are advantageously each located in a rectangular stabilizing box.

Each heat-exchange plate module is advantageously held in position by means of a suitable holder, for example by means of the rectangular stabilizing boxes, with a continuous lateral wall or, for example, by means of an angle construction.

In one embodiment, the rectangular stabilizing boxes of adjacent heat-exchange plate modules are sealed from one another. In this way, the reaction mixture cannot flow between the individual heat-exchange plate modules so as to bypass them.

The installation of cuboidal heat-exchange plate modules in a predominantly cylindrical reactor leaves relatively large free spaces at the edge next to the cylindrical wall. An inert gas can advantageously be fed into this space between the heat-exchange plate modules and the cylindrical wall of the reactor.

The cuboidal heat-exchange plate modules can be installed not only in cylindrical reactors but advantageously also in reactors having polygonal cross sections, in particular rectangular cross sections.

It is also possible for the heat-exchange plate modules not to have a cuboidal shape, but to be in the form of quarter cylinders, so that the interior space of a cylindrical reactor can be optimally utilized by appropriate arrangement of four quarter-cylindrical heat-exchange plate modules each having the same dimensions.

The fixed-bed catalyst is preferably installed in the gaps between the heat-exchange plates in zones having differing catalytic activities in particular by providing, in the flow direction of the reaction gas mixture, firstly an inert bed, subsequently a catalytically active zone and finally preferably a further inert bed. The length of the inert beds is in each case advantageously up to about 0.5 m and the length of the catalytically active zone is up to about 1.5 m, in particular in the range from 0.5 to 0.65 m.

Furthermore, it is advantageous for the fixed-bed catalyst to have a catalytic activity which changes in the flow direction of the reaction mixture in the region of the catalytically active zone, preferably so that the catalytic activity increases in the flow direction of the reaction gas mixture.

Catalyst particles having equivalent particle diameters in the range from 2 to 6 mm are particularly suitable for the process of the invention. The term equivalent particle diameter refers in a known manner to six times the ratio of volume to surface area of the particle.

The ratio of the width of the gaps between the heat-exchange plates to the equivalent particle diameters is preferably from 2 to 10, in particular from 3 to 8, particularly preferably from 3 to 5.

The process is particularly advantageously carried out at a superficial velocity of the reaction gas mixture of up to 4.5 m/s, preferably in the range from 1.0 to 2.5 m/s, particularly preferably about 2 m/s.

It is equally possible to pass the reaction gas mixture and the heat transfer medium through the gap or through the heat-exchange plates in countercurrent or in cocurrent, with cocurrent flow being preferred.

A particularly advantageous mode of operation is one in which the reaction mixture taken from the reactor for the oxidation of methanol vapor by the Formox process is introduced directly into an after-cooler which is preferably equipped with heat-exchange plates through which a cooling medium flows, with the reaction gas mixture preferably being cooled to a temperature below 150° C., preferably to a temperature below 110° C., in the after-cooler.

The process of the invention has the advantage that it alleviates the problems of the limited mechanical strength of fixed-bed catalysts customarily used in Formox processes. Furthermore, the fixed-bed catalysts located in gaps according to the process of the invention have a significantly lower tendency to become blocked compared to fixed catalyst beds which have been installed in catalyst tubes having a narrow tube diameter.

The invention is illustrated below with the aid of a drawing.

In the figures, identical reference numerals in each case denote identical or corresponding features.

In the individual figures:

FIG. 1A shows a preferred embodiment of a reactor for the process of the invention, cross section, with longitudinal section shown in FIG. 1B, FIG. 2A shows a cross section through a further, preferred embodiment of a reactor for the process of the invention, with longitudinal section shown in FIG. 2B, FIG. 3A shows a further, preferred embodiment in cross section, with longitudinal section through a heat-exchange plate shown in FIG. 3B, FIG. 4A shows another embodiment of a reactor for the process of the invention, with longitudinal section shown in FIG. 4B, FIG. 5 shows an embodiment of a reactor for the process of the invention, in longitudinal section, with after-cooler, FIG. 6 shows a further embodiment of a reactor with after-cooler, FIG. 7A depicts a cross section through an additional embodiment, with longitudinal section depicted in FIG. 7B and enlarged section in FIG. 7C, FIGS. 8A to 8C show different arrangements of heat-exchange plate modules, in cross section, FIG. 9 shows a cross section through a further preferred embodiment and FIGS. 10A and 10B depict the gaps between heat-exchange plates.

The cross-sectional depiction in FIG. 1A shows a section through a reactor 1 having parallel heat-exchange plates 2 which are arranged therein and leave the gap 5 free between the heat-exchange plates, with the gap 5 being charged with a solid catalyst. Inlet and outlet lines 3 and 4, respectively, are provided for the heat transfer medium circulating through the heat-exchange plates 2. The reaction mixture flows, for example, from the top downward through the reactor. However, the reverse flow direction, from the bottom upward, is likewise possible.

The longitudinal section shown in FIG. 1B illustrates the configuration of the heat-exchange plates 2 and the arrangement of inlet and outlet lines 3 and 4, respectively, in the reactor 1.

The cross section depicted in FIG. 2A shows a reactor 1 with heat-exchange plates 2 arranged radially therein and gaps 5 which are charged with the solid catalyst between the heat-exchange plates 2.

A dummy body is located in the central space 6 to improve the positioning of the heat-exchange plates 2 and to ensure essentially longitudinal flow of the reaction mixture through the reactor as indicated, in particular, by the arrows in the longitudinal section shown in FIG. 2B.

FIG. 3A shows a cross section through a further embodiment of a reactor for the process of the invention, without a dummy body in the central space 6. R denotes the radius of the reactor and r denotes the extension of each heat-exchange plate in the direction of the reactor radius R. The cross section through a heat-exchange plate 2 depicted in FIG. 3B shows rolled seams 7 to avoid dead zones in the flow of the heat transfer medium through the heat-exchange plates 2.

The cross section depicted in FIG. 4A shows a further embodiment having a peripheral channel 8 for collecting the reaction gas mixture and passing it on. The longitudinal section depicted in FIG. 4B illustrates the flow profile for the reaction gas mixture, in particular through the central space 6 and the peripheral channel 8, with the reaction gas mixture flowing radially through the gap 5 between the heat-exchange plates 2.

The longitudinal section depicted in FIG. 5 shows a reactor 1 with heat-exchange plates 2 and inlet and outlet lines 3 and 4, respectively, for the heat transfer medium, and also an after-cooler 10 which is likewise equipped with heat-exchange plates 2.

Reactor 1 and after-cooler 10 are located directly one after the other without caps located in between.

The longitudinal section depicted in FIG. 6 shows a reactor 1 with heat-exchange plates 2 and inlet and outlet lines 3 and 4, respectively, for the heat transfer medium, with downstream after-cooler 10 which is likewise equipped with heat-exchange plates 2, where the reactor 1 and the after-cooler 10 each have two caps.

The cross section depicted in FIG. 7 shows an assembly of eight heat-exchange plate modules 9 in a cuboidal reactor 1, with longitudinal section depicted in FIG. 7B and enlarged section to show the heat-exchange plates 2 and the gap 5 in FIG. 7C.

FIGS. 8A to 8C show assemblies of 4, one and 7 heat-exchange plate modules 9 in a cylindrical reactor 1, in cross section.

Figure 1A:
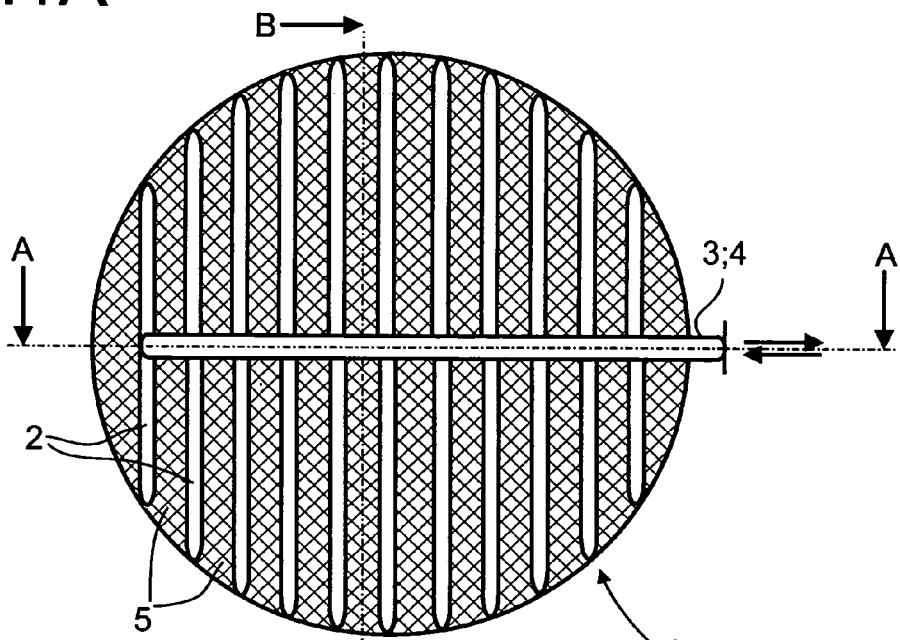
Figure 1B:
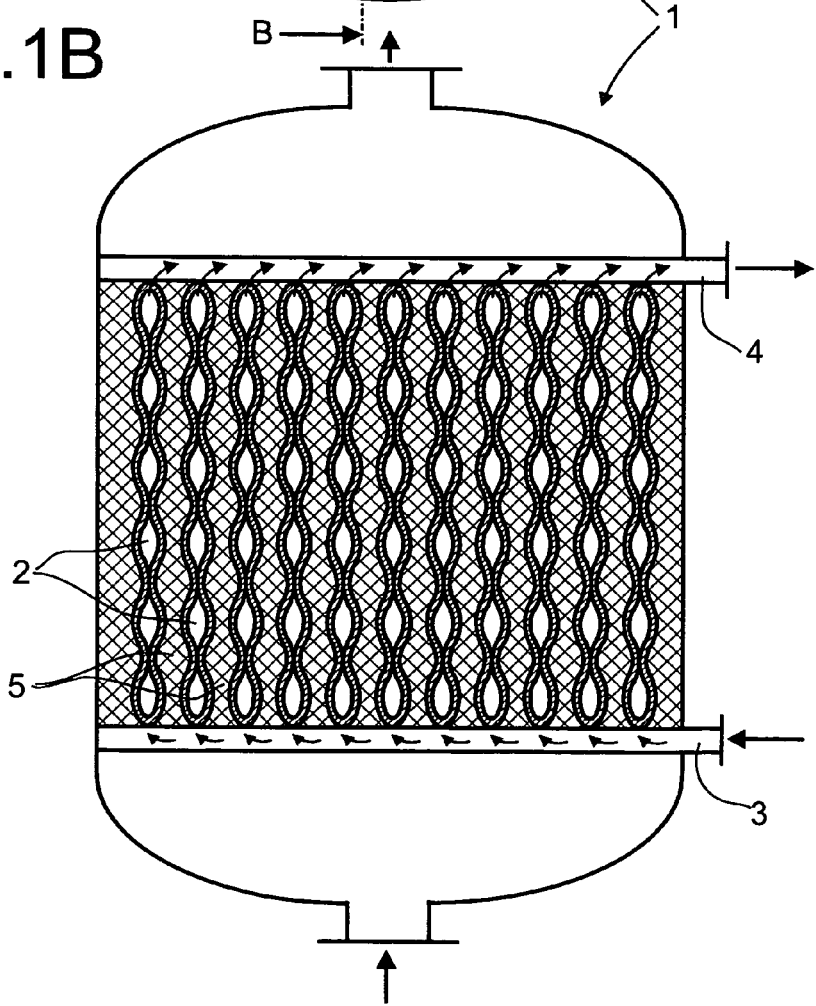
Figure 2A:
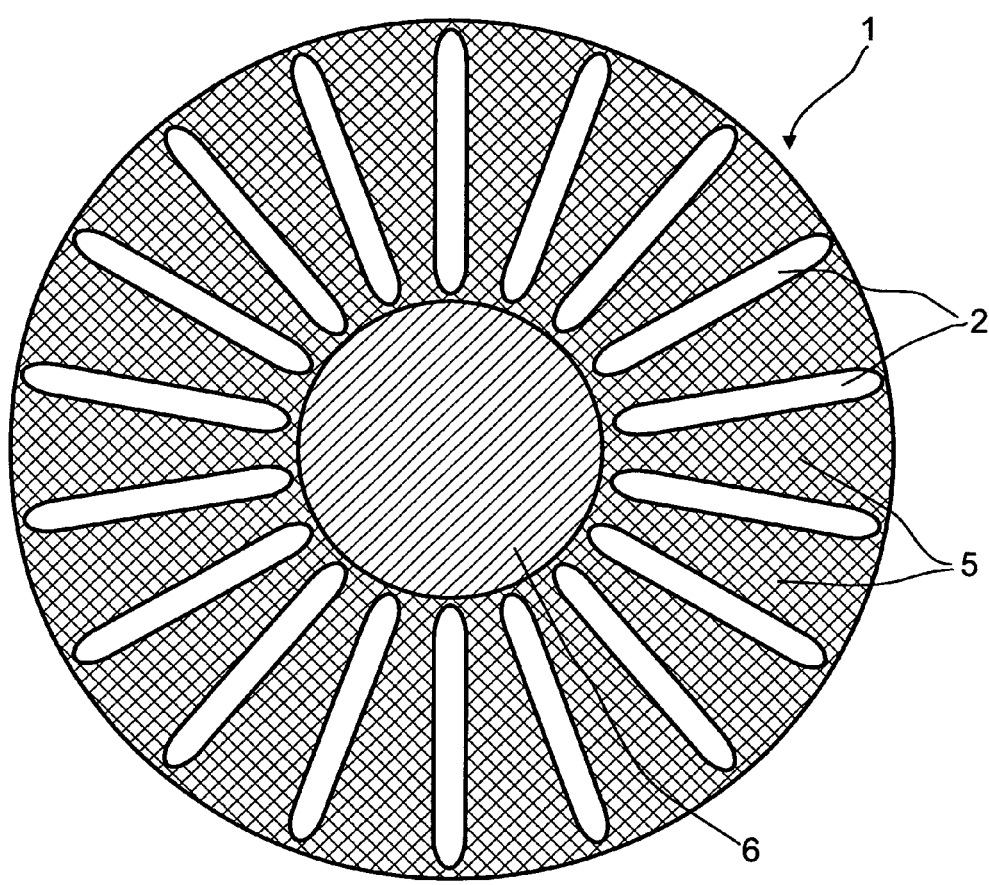
Figure 2B:
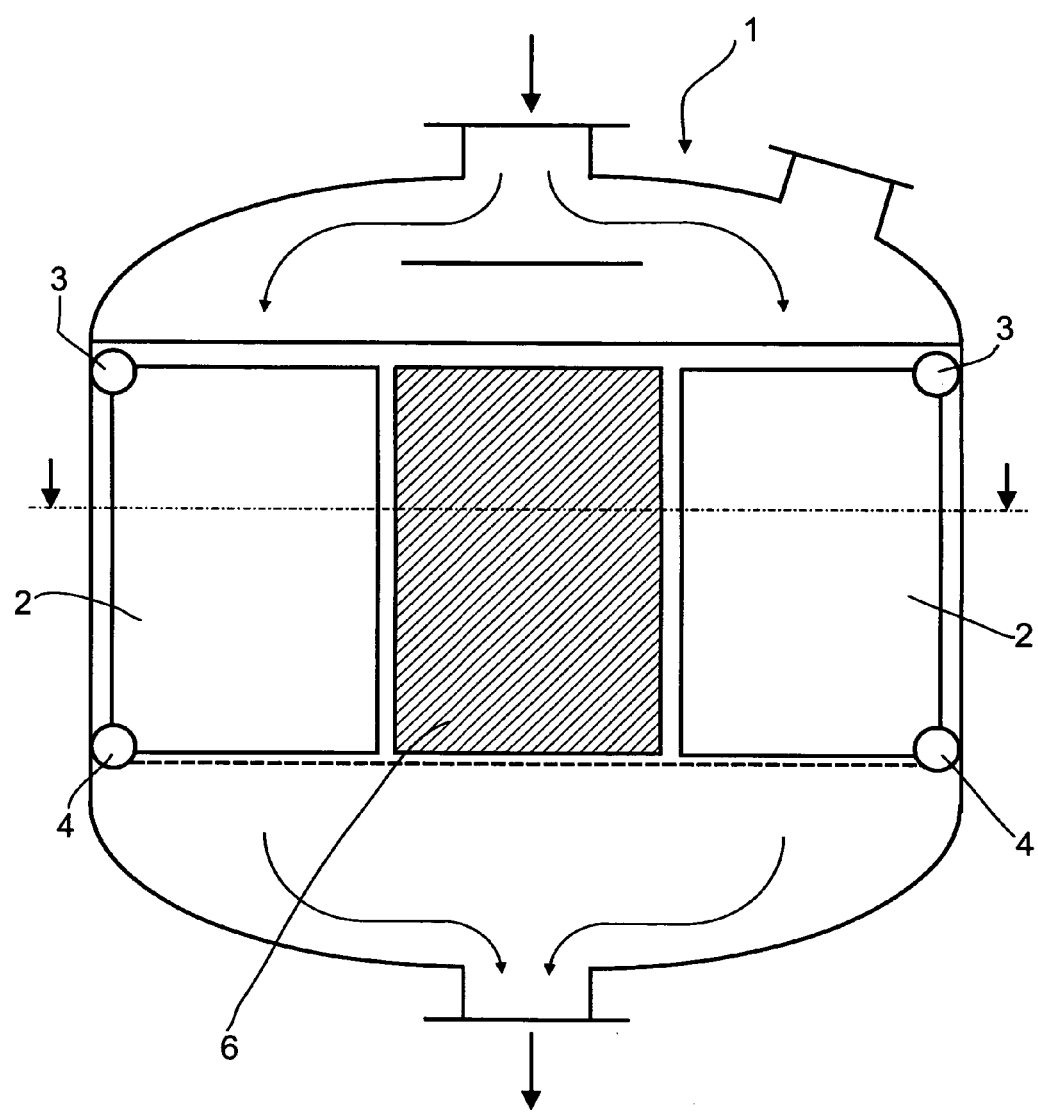
Figure 3A:
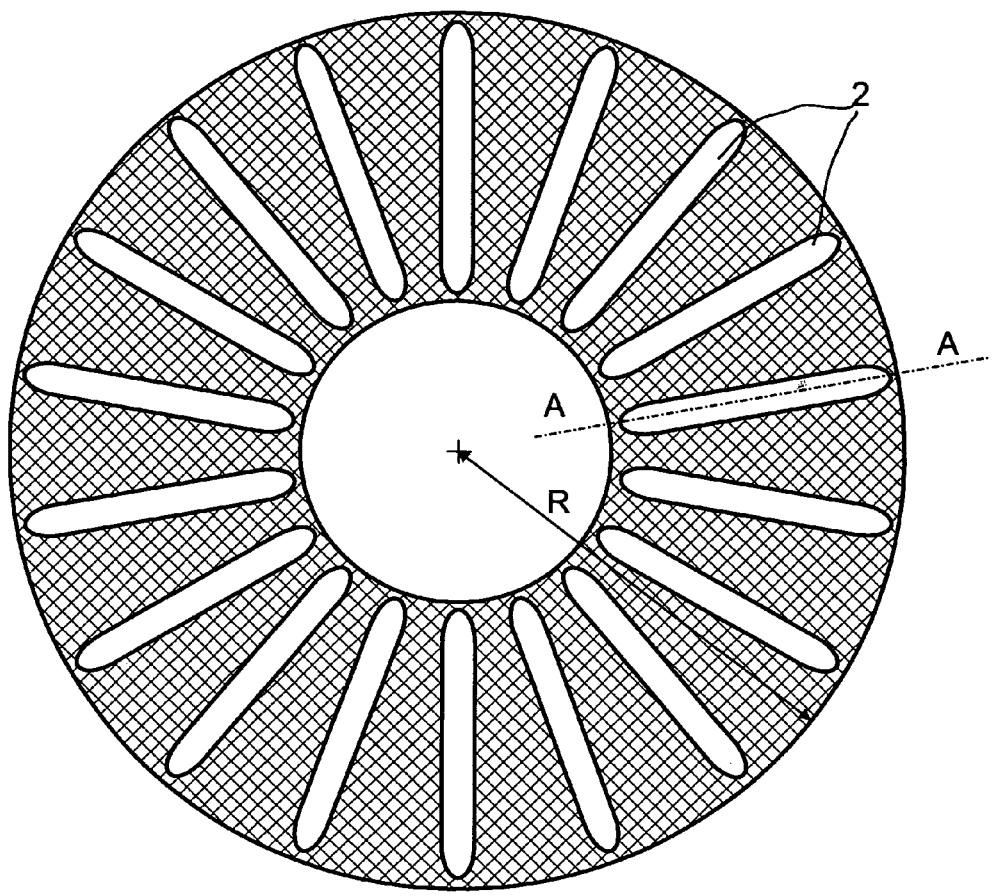
Figure 3B:
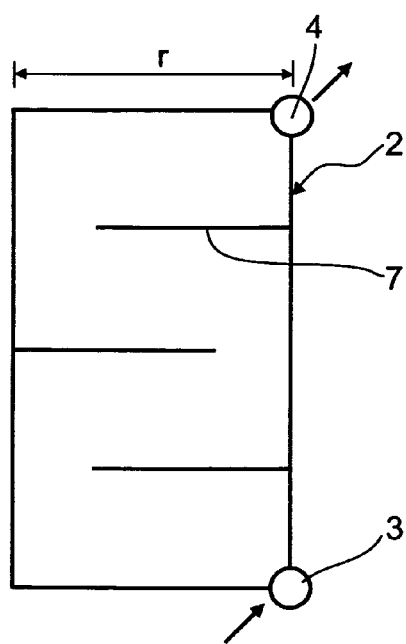
Figure 4B:
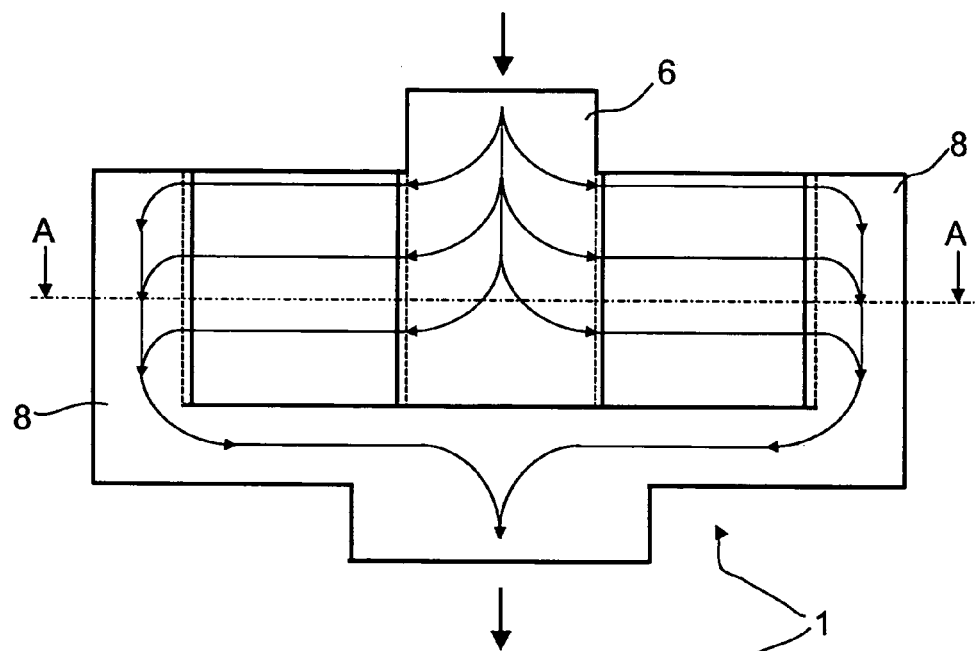
Figure 4A:
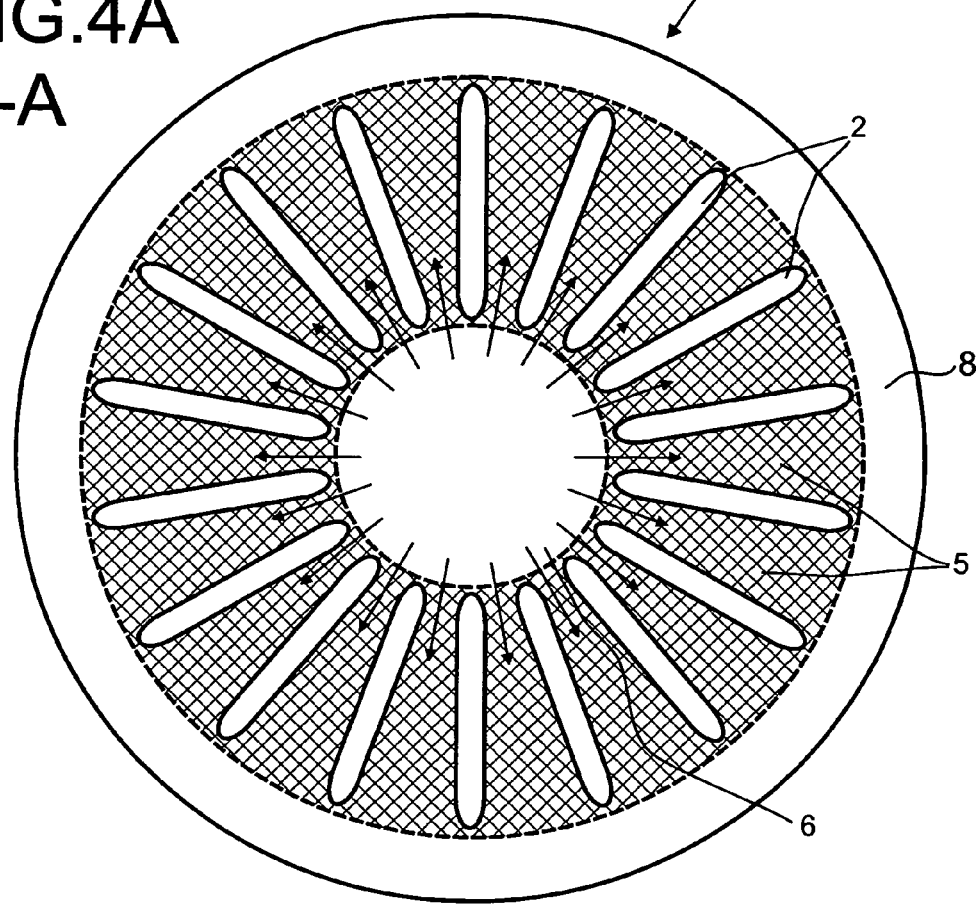
Figure 5:
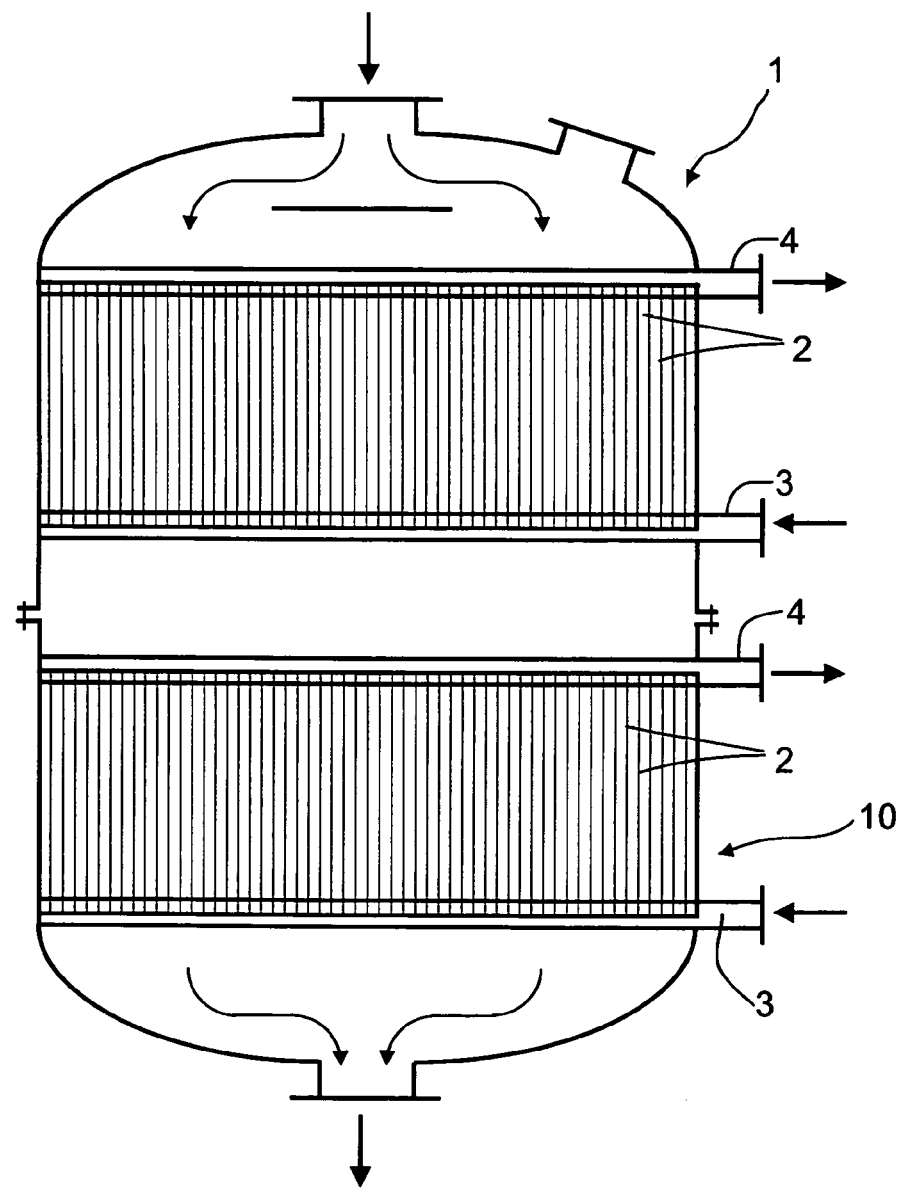
Figure 6:
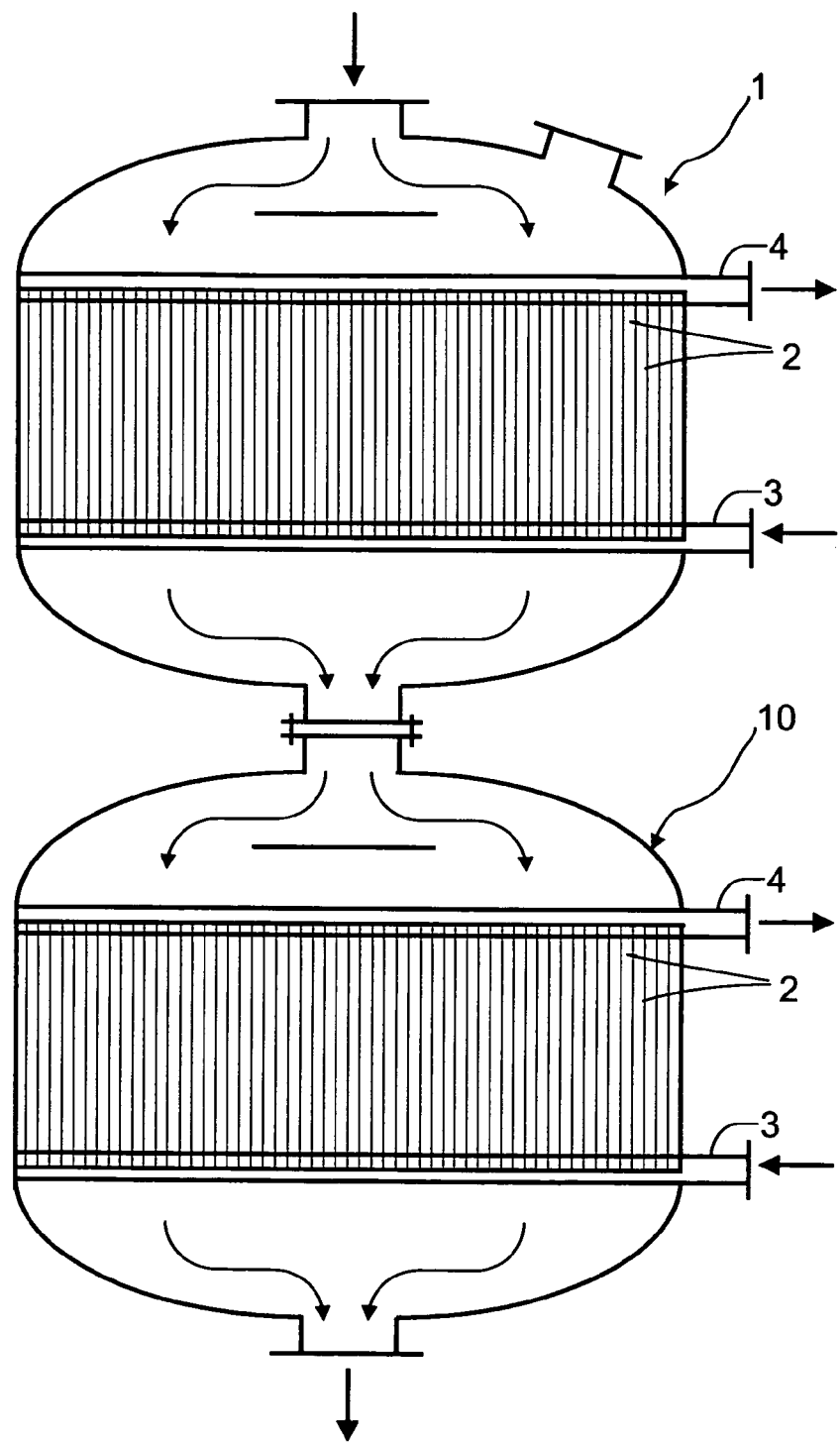
Figure 7A:
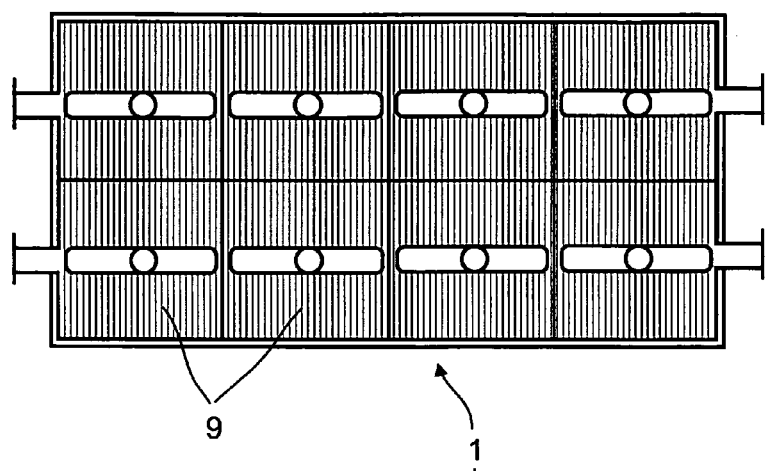
Figure 7B:
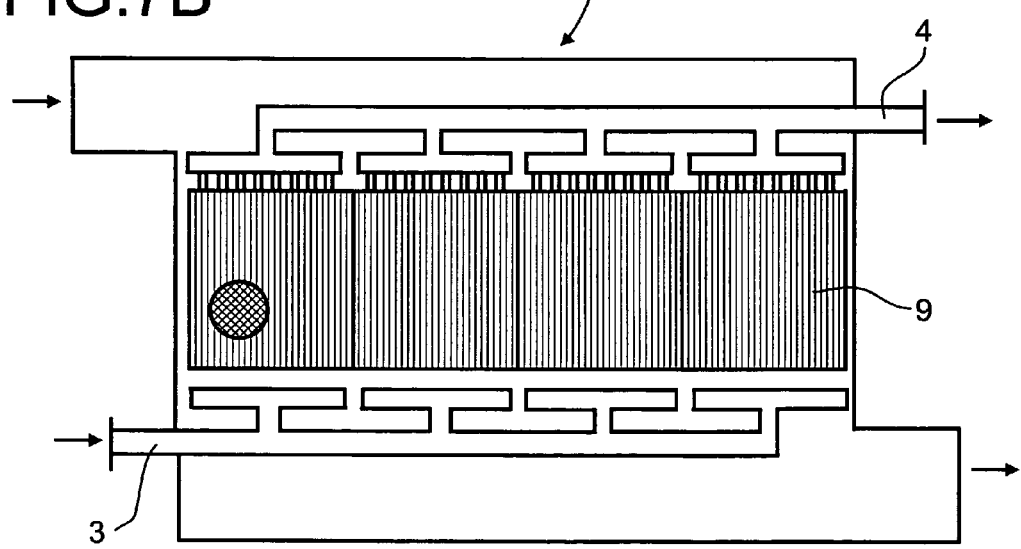
Figure 7C:
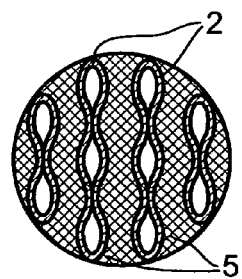
Figure 8A:
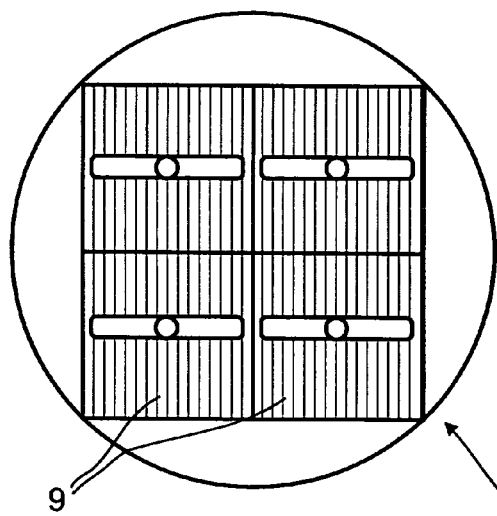
Figure 8B:
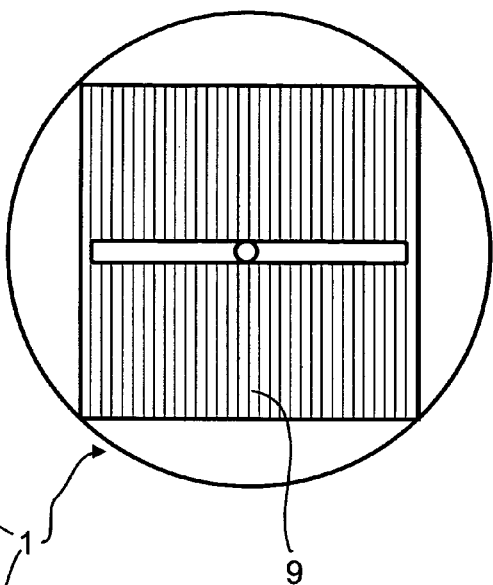
Figure 8C:
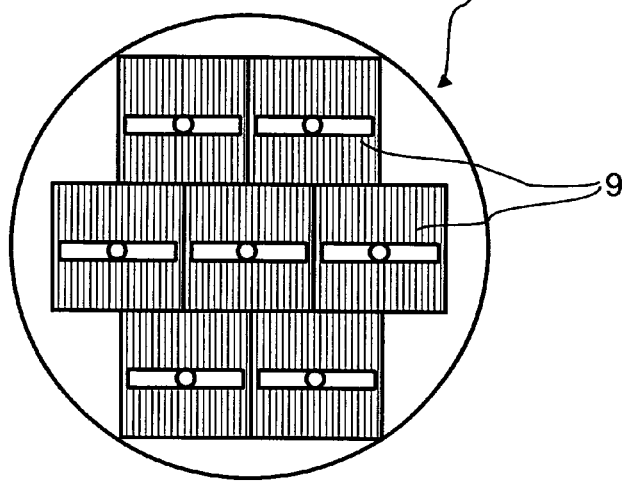
Figure 9:
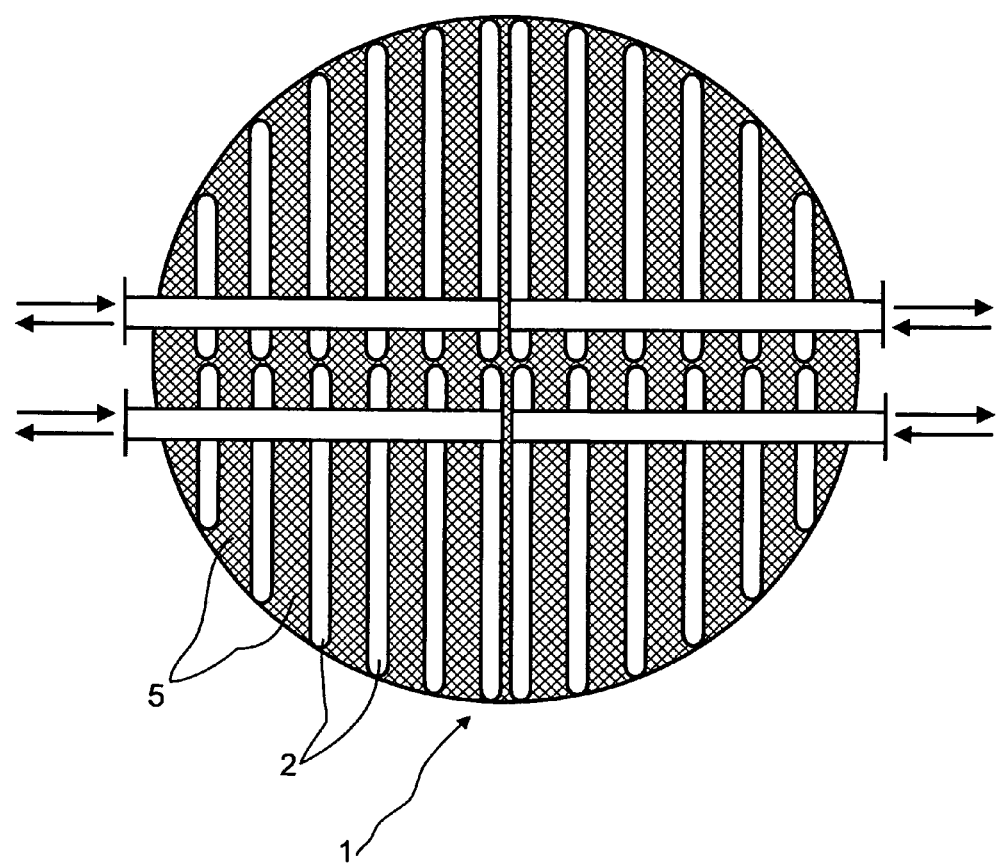
FIG. 9 shows a cross section through a reactor 1 with four heat-exchange plate modules 2 each having a cross section in the shape of a quarter circle.
Figure 10A:
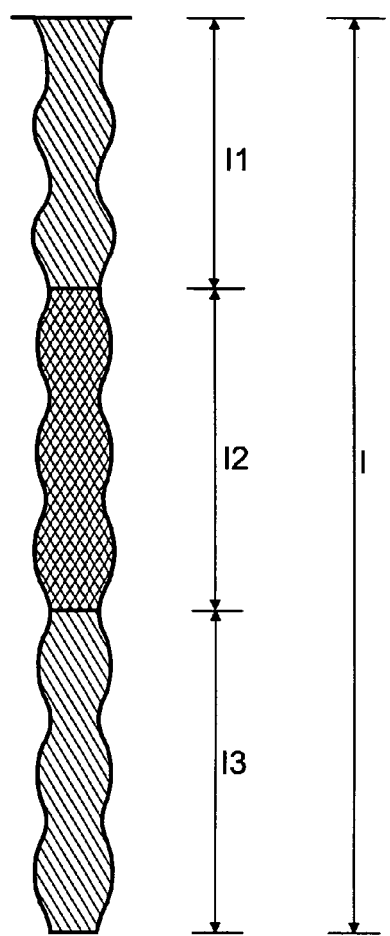
FIG. 10A shows a longitudinal section through a gap 5 having three superposed zones, with the two outer, in each case obliquely hatched zones being charged with inert material and the middle, cross-hatched zone being charged with the fixed-bed catalyst.
Figure 10B:
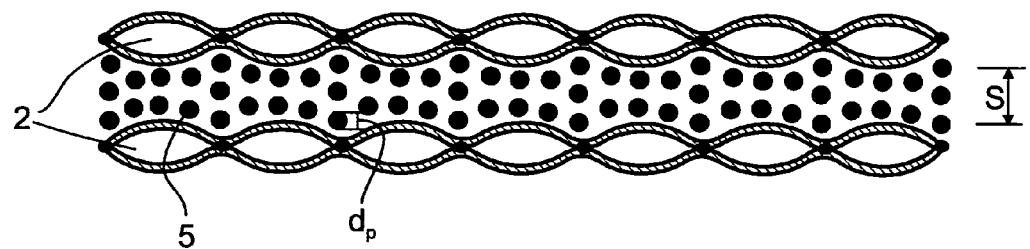

FIG. 10B illustrates the configuration of the heat-exchange plates 2 and the gap 5 located between them, with fixed-bed catalyst having an equivalent particle diameter $d_p$ present therein. It can be seen from the figure that the width s of the gap 5 is the smallest distance between two immediately adjacent heat-exchange plates 2.

The invention claimed is:

1. A process for preparing formaldehyde by gas-phase oxidation of methanol vapor by means of a gas stream comprising molecular oxygen in the presence of a fixed-bed catalyst comprising iron and molybdenum, wherein the process is carried out in a reactor having heat-exchange plates which are arranged in the longitudinal direction of the reactor and have a spacing between them and through which a heat transfer medium flows, inlet and outlet facilities for the heat transfer medium to the heat-exchange plates and also gaps between heat-exchange plates in which the fixed-bed catalyst is present and into which the methanol vapor and the gas stream comprising molecular oxygen are passed, wherein the reactor is cylindrical and the heat-exchange plates are arranged radially to leave a central space and a peripheral channel free in the cylindrical reactor and the gas stream comprising methanol vapor and molecular oxygen is fed radially into the gap between the heat-exchange plates.

2. A process according to claim 1, wherein the radial extension (r) of the heat-exchange plates is from 0.1 to 0.95 of the reactor radius (R).

3. A process according to claim 1, wherein the reactor is made up of two or more, in particular detachable reactor sections and each reactor section is preferably equipped with a separate heat exchange medium circuit.

4. A process according to claim 1, wherein the heat-exchange plates are each made up of two rectangular metal sheets which are joined on their longitudinal sides and ends by rolled seam welding and the margin of the metal sheets projecting beyond the rolled seam is separated off at the outer edge of the rolled seam or in the rolled seam itself.

5. A process according to claim 1, wherein the fixed-bed catalyst in the gaps is arranged in zones having a differing catalytic activity.

6. A process according to claim 5, wherein the fixed-bed catalyst has a catalytic activity which changes in the flow direction of the reaction gas mixture in the region of the catalytically active zone.

7. A process according to claim 1, wherein a fixed-bed catalyst made up of particles having an equivalent particle diameter $d_p$ in the range from 2 to 6 mm is used.

8. A process according to claim 1, wherein the width (s) of the gap is in the range from 8 to 50 mm and the ratio of the width of the gap to the equivalent particle diameters ($s/d_p$) is from 2 to 10.

9. A process according to claim 1, wherein the superficial velocity of the reaction gas mixture in the gaps is up to 4.5 m/s.

10. A process according to claim 1, wherein the reaction gas mixture is taken from the reactor, introduced directly into an after-cooler.

11. A process according to claim 1, wherein the reaction gas mixture and the heat transfer medium are conveyed in cocurrent through the reactor.

12. A process for preparing formaldehyde by gas-phase oxidation of methanol vapor by means of a gas stream comprising molecular oxygen in the presence of a fixed-bed catalyst comprising iron and molybdenum, wherein the process is carried out in a reactor having heat-exchange plates which are arranged in the longitudinal direction of the reactor and have a spacing between them and through which a heat transfer medium flows, inlet and outlet facilities for the heat transfer medium to the heat-exchange plates and also gaps between heat-exchange plates in which the fixed-bed catalyst is present and into which the methanol vapor and the gas stream comprising molecular oxygen are passed, wherein the heat-exchange plates are arranged parallel to one another in the reactor.

13. A process according to claim 12, wherein the reactor is equipped with one or more cuboidal heat-exchange plate modules which are each made up of two or more rectangular heat-exchange plates which are arranged parallel to one another so as to leave a gap between them.

14. A process according to claim 12, wherein the reactor has four quarter-cylindrical cuboidal heat-exchange plate modules each having identical dimensions.

15. A process according to claim 13, wherein the reactor has two or more cuboidal heat-exchange plate modules each having identical dimensions.

16. A process according to claim 15, wherein the reactor has 4, 7, 10 or 14 heat exchange plate modules.

17. A process according to claim 13, wherein the reactor is cylindrical and an inert gas is fed into the space between the heat-exchange plate modules and the cylindrical wall of the reactor.

* * * * *